US006294542B1

(12) United States Patent
Lee et al.

(10) Patent No.: US 6,294,542 B1
(45) Date of Patent: Sep. 25, 2001

(54) PYRIMIDINONE COMPOUNDS, PHARMACEUTICAL COMPOSITIONS CONTAINING THE COMPOUNDS AND THE PROCESS FOR PREPARING THE SAME

(75) Inventors: Jae-hyoung Lee; Kyung-jin Jang, both of Ansan; Byoung-wug Yoo, Kyunggi-do; Ji-han Kim, Seoul; Jae-seog Kang, Kunpo; Sang-lin Kim, Seoul, all of (KR)

(73) Assignee: Boryung Pharmaceutical Co. Ltd., Seoul (KR)

( * ) Notice: Subject to any disclaimer, the term of this patent is extended or adjusted under 35 U.S.C. 154(b) by 0 days.

(21) Appl. No.: 09/446,254

(22) PCT Filed: Apr. 26, 1999

(86) PCT No.: PCT/KR99/00198

§ 371 Date: Dec. 20, 1999

§ 102(e) Date: Dec. 20, 1999

(87) PCT Pub. No.: WO99/55681

PCT Pub. Date: Nov. 4, 1999

(30) Foreign Application Priority Data

Apr. 25, 1998 (KR) .................................................. 98-14821

(51) Int. Cl.$^7$ ..................... C07D 239/36; C07D 239/46; C07D 401/06; A61K 31/513
(52) U.S. Cl. .......................... 514/269; 540/601; 540/553; 540/575; 540/544; 540/470; 540/467; 514/235.8; 514/227.8; 514/183; 514/211.01; 514/211.08; 514/211.15; 514/217.06; 514/218; 514/274; 544/58.5; 544/123; 544/295; 544/296; 544/311; 544/319; 544/310

(58) Field of Search ...................................... 514/269, 275; 544/311, 319, 296, 58.5; 511/218, 211.08, 227.8; 540/601, 544

(56) References Cited

U.S. PATENT DOCUMENTS

| 5,100,897 | 3/1992 | Allen et al. .......................... 514/269 |
| 5,312,920 | 5/1994 | Chekroun et al. ................... 544/319 |
| 5,330,987 | 7/1994 | Allen et al. .......................... 514/258 |
| 5,371,233 | 12/1994 | Daumas et al. ...................... 548/250 |
| 5,430,149 | 7/1995 | Chekroun et al. ................... 544/319 |
| 5,869,476 | 2/1999 | Paik ..................................... 514/183 |

FOREIGN PATENT DOCUMENTS

| 419048 | 3/1991 | (EP) . |
| 418614 | 4/1992 | (EP) . |
| 550313 | 7/1993 | (EP) . |
| 561664 | 9/1993 | (EP) . |
| 607077 | 7/1994 | (EP) . |
| WO 96/08476 | 3/1996 | (WO) . |

Primary Examiner—John M. Ford
(74) Attorney, Agent, or Firm—Fish & Richardson P.C.

(57) ABSTRACT

The present invention relates to a novel pyrimidinone compounds and the pharmaceutical acceptable salts thereof having remarkable antagonistic action against angiotensin II receptor, thereby, being useful in treating cardiovascular disease caused by binding angiotensin II to its receptor.

12 Claims, No Drawings

PYRIMIDINONE COMPOUNDS, PHARMACEUTICAL COMPOSITIONS CONTAINING THE COMPOUNDS AND THE PROCESS FOR PREPARING THE SAME

This is a 317 of pct/kR 99/00198, filed Apr. 26, 1999.

BACKGROUND OF THE INVENTION

1. Technical Field

The present invention relates to a novel pyrimidinone compounds and the pharmaceutically acceptable salts thereof This invention also relates to a process for preparing the novel pyrimidinone compounds and a pharmaceutical composition containing the pyrimidinone compounds.

2. Background Art

Pyrimidinone derivatives according to this invention and the pharmaceutically acceptable salts thereof are useful as antagonists against angiotensin II, especially, in treatment of cardiovascular diseases caused by binding angiotensin II to its receptor.

Renin-angiotensin system plays a central role in the regulation of blood pressure in human body. Angiotensin II, consisting of eight amino acids, is produced through the cleavage of angiotensin I by angiotensin converting enzyme (ACE) localized on the arterial blood vessels of lung. Angiotensin II interacts with specific receptors present in blood vessels, smooth muscle, kidney, and adrenal gland, to induce the blood pressure and the electrolyte concentration to increase.

Thus, several antagonistic compounds have been developed to inhibit the effect of angiotensin II by selectively blocking its receptors.

Conventionally, peptide antagonists analogous to angiotensin II have been proposed, but their clinical applications have been limited because of their short half-life, oral inertia as well as local increase of blood pressure.

Recently, lots of researches have been reported in connection with non-peptide angiotensin II antagonists (U.S. Pat. No. 4,207,324, 4,340,598, 4,576,958, 4,582,847, and 4,880,804; European Patent Laying-Open Publication Nos. 028,834, 245,637, 253,310, 291,969, 323,841 and 324,377). European Patent Laying-Open Publication Nos. 028,834 and 253,310 disclose Imidazole derivatives substituted by biphenyl (for example, Losartan) and European Patent Laying-Open Publication No. 245,637, imidazopyridine derivatives (for example, L158,809) as potent angiotensin II antagonists.

In European Patent Laying-Open Publication Nos. 407, 342, 419,048 and 445,811, pyrimidinone compounds similar to the compounds of this invention in their 6 membered heterocyclic ring structure are disclosed, including nitrogen which is very different from the 5 membered imidazole derivatives. But, the pyrimidinone compounds have lower activities than the imidazole derivatives described in the above mentioned application.

In the meantime, the inventors of this invention have filed a PCT application (WO 96-08476) for a novel compounds having noticeably high activities (in vitro (rabbit aorta), 60~70% inhibition for $10^{-8}$ to $10^{-9}$ mole in vitro blood vessel dilation study) which is 50 times higher than or equal to imidazole derivatives known in the above mentioned application.

DISCLOSURE OF INVENTION

In search of novel pyrimidinone compounds, the inventors of this invention have developed novel pyrimidinone derivatives of thioamid and amidine, which are superior to pyrimidinone derivatives disclosed in the prior art or the said imidazole derivatives in the activities and active time periods.

An object of the invention, therefore, is to provide with novel pyrimidinone derivatives and the pharmaceutically acceptable salts thereof which inhibit the action of angiotensin II effectively with high activities.

In order to achieve the aforementioned objects, the present invention provides with pyrimidinone derivatives and the pharmaceutically acceptable salts thereof having the general formula (I):

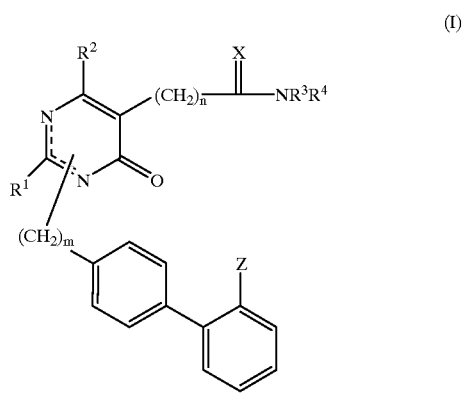

wherein:

$R^1$ is $C_1$~$C_4$ normal or side chain alkyl, cycloalkyl, $C_1$~$C_4$ alkylalkoxy or $C_1$~$C_4$ alkylmercapto;

$R^2$ is H, halogen, $C_1$~$C_4$ alkyl, aryl or arylalkyl;

$R^3$, $R^4$ is same or different H, $C_1$~$C_4$ normal or side chain alkyl, cycloalkyl, aryl, arylalkyl, $C_1$~$C_4$alkyl or arylcarbonyl, $C_1$~$C_4$ alkoxycarbonyl, or substituted aminocarbonyl, being optionally substituted by H, halogen, hydroxy, $C_1$~$C_4$ alkoxy, amino, alkylamino or dialkylamino (each alkyl having $C_1$~$C_5$), $C_1$~$C_4$ alkoxycarbonyl, carboxy, or substituted aminocarbonyl, $R^3$ and $R^4$ are together with N atom forming 4 to 8 membered heterocyclic ring, which can be further substituted with one or two substituents selected from the group consisting of cycloalkyl, aryl or arylalkyl, halogen, hydroxy, and $C_1$~$C_4$ alkoxy, amino, alkylamino or dialkylamino (each alkyl residue having $C_1$~$C_5$), $C_1$~$C_4$ alkoxycarbonyl, carboxy or substituted aminocarbonyl, and $C_1$~$C_4$ normal or side chain alkyl being optionally substituted by H; and the heterocyclic ring can further include —O—, —S—, —SO—, —SO$_2$—, >N—R$^5$;

$R^5$ is H, $C_1$~$C_4$ alkyl, aryl, arylalkyl, substituted alkenyl, pyridyl, pyrimidyl, $C_1$~$C_4$ alkyl or arylcarbonyl, $C_1$~$C_4$ alkoxy carbonyl, substituted aminocarbonyl, CN or SO$_2$NR$^3$R$^4$;

X is S or >N—R$^5$; and

Z is CN, COOR$^3$, SO$_2$NR$^3$R$^4$ or tetrazol-5-yl radical having below general formula,

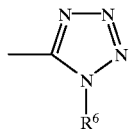 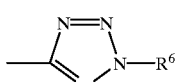

wherein $R^6$ is H, t-butyl or triphenylmethyl;

m is 1 or 2; and n is 1, 2, 3, 4, 5 and 6.

The pyrimidinone compounds according to the present invention and pharmaceutically acceptable salts thereof exhibit remarkable activities.

Preferable are such compounds wherein $R^1$ is ethyl, n-propyl, n-butyl, cyclopropyl, etoxy or propoxy; $R^2$ is H, halogen or $C_1 \sim C_4$ normal or side chain alkyl; $R^3$ and $R^4$ are same or different H, methyl, ethyl, propyl or butyl, or $R^3$ and $R^4$ are together with N atom forming 4 to 8 membered cyclic ring, which can be further substituted with one or two substituents selected from the group consisting of cycloalkyl, aryl or arylalkyl, halogen, hydroxy, $C_1 \sim C_4$ alkoxy, amino, alkylamino, or dialkylamino (each alkyl residue having $C_1 \sim C_5$), $C_1 \sim C_4$ alkoxycarbonyl, carboxy and substituted aminocarbonyl, and $C_1 \sim C_4$ normal or side chain-alkyl being optionally substituted by H; and the heterocyclic ring can further include —O—, —S—, —SO—, —SO$_2$—, >N—$R^5$; $R^5$ is H, $C_1 \sim C_4$ alkyl, aryl, arylalkyl, substitutedalkenyl, pyridyl, pyrimidyl, $C_1 \sim C_4$ alkyl or arylcarbonyl, $C_1 \sim C_4$ alkoxy carbonyl, substituted aminocarbonyl, CN or SO$_2$NR$^3$R$^4$, more preferably H, $C_1 \sim C_4$ alkyl, $C_1 \sim C_4$ alkoxy carbonyl, substituted aminocarbonyl, CN or SO$_2$NR$^3$R$^4$; X is S or >N—$R^5$; Z is tetrazol-5-yl radical; and m is 1.

Best Mode for Carrying Out the Invention

The Pharmaceutically acceptable salts of the invention include inorganic salts obtainable by reacting corresponding pyrimidinone compounds (I) with hydroxides of alkali metal or alkaline earth metals such as sodium hydroxide, potassium hydroxide, calcium hydroxide or magnesium hydroxide, potassium hydroxide, calcium hydroxide or magnesium hydroxide, carbonate of alkali metal or alkaline earth metals such as sodium carbonate, potassium carbonate, calcium carbonate or magnesium carbonate, or alcoholate of alkali metal or alkaline earth metals such as sodium, potassium, calcium or magnesium, and organic salts obtainable by reacting with organic amine in H$_2$O, alcohols such as methanol, ethanol, isopropyl alcohol, t-butyl alcohol, etc., tetrahydrofuran, or the mixture thereof.

The compound (I) can be prepared by reacting formula (I) of below-mentioned compound (II).

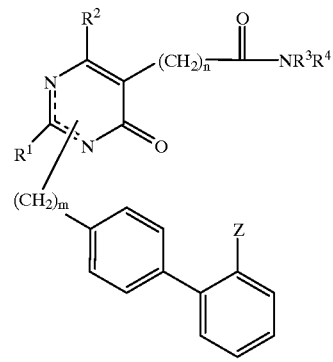

Reacting Formula I

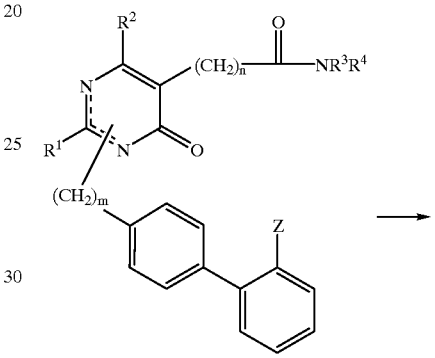

Compound formula II

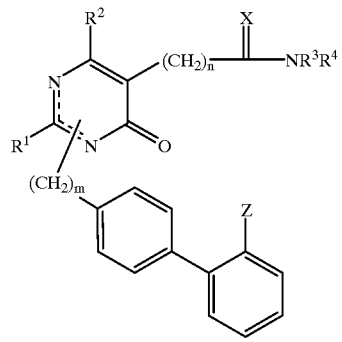

Compound formula I wherein $R^1$, $R^2$, $R^3$, $R^4$, X, Z, m, and n have the meaning defined as above.

Starting materials of the compound of formula II may be prepared by the process which has been disclosed in the PCT application Laying-Open Publication No WO 96-08476 by the present inventors. The compound of formula I, in which X is S, may be easily prepared by reacting compound (II) with P$_4$S$_{10}$, bis(tricyclohexyltartar)sulfide or Lawesson's reagent in a dissolvent selected among benzen, dichloromethan or tetrahydrofuran. On the other hand, the compound of formula I, in which X is NR$^5$; may be easily prepared from the compound (II) by adding substituted amine after preparation of iminium intermediate by using a reagent such as oxalylchloride, phosphorous oxychloride or ehtyl chloroformate in a dissolvent selected among benzene, ether or tetrahydrofuran.

Representative compounds of the invention are as follows, wherein name in the parentheses respectively after the compounds represent tentative name used through the specification.

2-n-butyl-5-aminothiocarbonylmethyl-6-methyl-3-[[2'-(1H-tetrazol-5-yl)biphenyl-4-yl]methyl]-pyrimidine-4(3H)-one (Compound 1), 2-n-butyl-5-dimethylaminothiocarbonylmethyl-6-methyl-3-[[2'-(1H-tetrazol-5-yl) biphenyl-4-yl] methyl]-pyrimidine-4(3H)-one (Compound 2), 2-n-butyl-5-diethylaminothiocarbonylmethyl-6-methyl-3-[[2'-(1H-tetrazol-5-yl)biphenyl-4-yl]methyl]-pyrimidine-4(3H)-one (Compound 3), 2-n-butyl-5-heptamethyleniminothiocarbonyl-methyl-6-methyl-3-[[2'-(1H-tetrazol-5-yl)biphenyl-4-yl]methyl]-pyrimidine-4(3H)-one (Compound 4), 2-n-butyl-5-thiomorpholynothiocarbonylmethyl-6-methyl-3-[[2'-(1H-tetrazol-5-yl)-biphenyl-4-yl]methyl]-pyrimidine-4(3H)-one (Compound 5), 2-n-butyl-5-morpholynothiocarbonylmethyl-6-methyl-3-[[2'-(1H-tetrazol-5-yl) -biphenyl-4-yl]methyl)]-pyrimidine-4(3H)-one (Compound 6), 2-n-butyl-5-piperidinothiocarbonylmethyl-6-methyl-3-[[2 '-(1H-tetrazol-5-yl)-biphenyl-4-yl]methyl]-pyrimidine-4(3H)-one (Compound 7), 2-n-butyl-5-pyrrolidinothiocarbonylmethyl-6-methyl-3-[[2'-1H-tetrazol-5-yl)-biphenyl-4-yl]methyl]-pyrimidin-4(3H)-one (Compound 8), 2-n-butyl-5-azetidinothiocarbonylmethyl-6-methyl-3-[[2 1'-1H-tetrazol-5-yl) -biphenyl-4-yl]methyl]-pyrimidine-4(3H)-one (Compound 9), 2-n-butyl-5-(2'-aminothiocarbonylethyl)-6-methyl-3-[[2'-(1H-tetrazol-5-yl)-biphenyl-4-yl]methyl ]-pyrimidine-4(3H)-one (Compound 10), 2-n-butyl-5-(2'-dimethylaminothiocarbonylethyl)-6-methyl-3-[[2'-(1H-tetrazol-5-yl)-biphenyl-4-yl]methyl]-pyrimidine-4(3H)-one (Compound 11), 2-n-butyl-5-(2'-diethylaminothiocarbonylethyl)-6-methyl-3-[[2'-(1H-tetrazol-5-yl)-biphenyl-4-yl]methyl]-pyrimidine-4(3H)-one (Compound 12), 2-n-butyl-5-(2'-thiomorpholynothiocarbonylethyl)-6-methyl-3-[[(2'-(1H-tetrazol-5-yl)-biphenyl-4-yl]methyl]-pyrimidine-4(3H)-one (Compound 13), and 2-n-butyl-5-(2'-morpholynothiocarbonylethyl)-6-methyl-3-[[2'-(1H-tetrazol-5-yl)-biphenyl-4-yl]methyl]-pyrimidine-4(3H)-one (Compound 14).

A compound of formula I and the pharmaceutically acceptable salts thereof may be administered orally or parenterally in a conventional dosage from such as tablet, capsule, powder, troches, dry mixes, ointment, suspension or solution prepared according to conventional pharmaceutical practices.

The compounds of formula I, etc. can be administered at a dosage of from about 40 mg/kg to about 100 mg/kg preferably of body weight per day.

The compounds of the present invention have extremely low toxicity. The $LD_{50}$ in mice is in excess of 5000 mg/kg of body weight, as shown in the experimental test 2.

The present invention will be described in more detail with reference to preferred embodiments hereinafter and as such are not to be considered as limiting the scope of the present invention.

EXAMPLE 1

2-n-butyl-5-aminothiocarbonylmethyl-6-methyl-3-[[2'-(1H-tetrazol-5-yl)biphenyl-4-yl]methyl]-pyrimidine-4(3H)-one (Compound 1),

PROCESS 1

1.2g of 2-n-butyl-5-aminocarbonylmethyl-6-methyl-3-[[2'-(N-triphenylmethyltetrazol-5-yl)biphenyl-4-yl]methyl]-pyrimidine-4(3H)-one (WO 96-08476) were dissolved in 20 mL of benzene at room temperature, and 600 mg of Lawesson's reagent was added thereto. After heating the mixture and stirring it for 5 hours, the mixture was cooled at room temperature, unnecessary solid material was filtrated therefrom, and concentrated under the reduced pressure. The residue was separated and purified on a chromatography using acetate/hexane (1:2) to obtain 700 mg (57%) of intermediate product After dissolving the intermediate product in 100 mL of tetrahydrofuran, the solution was cooled at 0–5° C. and 5 ml of 4M hydrochloric acid solution was slowly added thereto. The solution was refluxed for 4 hour and then neutralized by adding 4M sodium hydroxide solution $H_2O$ layer was saturated with solid sodium chloride and extracted three times by using chloroform. The organic solution thus obtained was washed with saturated brine, and then dried and concentrated with anhydride magnesium sulfate. The residue was eluted on a chromatography using chloroform and chloroform/methanol (9:1) to yield 310 mg (65%) of the compound 1.

PROCESS 2

500 mg of 2-n-butyl-5-aminocarbonylmethyl-6-methyl-3-[[(1H-tetrazol-5-yl)biphenyl-4-yl]methyl]-pyrimidine-4(3H)-one (WO 96-08476) were dissolved in 20mL of tetrahydofuran at room temperature, and 400 mg of Lawesson's reagent was added thereto. After heating the mixture and stirring it for 5 hours, the mixture was cooled at room temperature, unnecessary solid material was filtrated therefrom, and concentrated under the reduced pressure. The residue was separated and purified on a chromatography using chloroform and chloroform/methanol (9:1) to yield 200 mg (45%) of the compound 1.

M.P.: 94.6~102.3° C.;

TLCR$_f$: 0.33(5% MeOH in CHCl$_3$); 1H NMR (DMSO-d$_6$): δ 0.83(t,3H), 1.19~1.40(m,2H), 1.48~1.65(m,2H), 2.21 (s,3H), 2.60(s,2H), 3.35(s,2H), 5.27(s,2H), 7.01~7.09(m, 4H), 7.39~7.61(m,4H), 6.83(s,1H), 7.07(s,4H), 7.30(s,1H), 7.40~7.68(M,4H).

Through the same process, the following compounds were prepared.

EXAMPLE 2

2-n-butyl-5-dimethylaminothiocarbonylmethyl-6-methyl-3-[[2'-(1H-tetrazol-5-yl)biphenyl-4-yl]methyl]-pyrimidine-4(3H)-one (Compound 2), M.P. 96.8~101.8° C.; TLCR$_f$: 0.28(5% MeOH in CHCl$_3$); 1H NMR(CDCl$_3$): δ 0.89(t,3H), 1.28~1.45(m,2H), 1.58~1.74(m,2H), 2.26(s,3H), 2.63(t,2H), 3.44(s,3H), 3.46 (s,3H), 3.77(s,2H), 5.22(s,2H), 7.07(s,5H), is 7.33~7.60(m, 3H), 7.94(dd,1H).

EXAMPLE 3

2-n-butyl-5-diethylaminothiocarbonylmethyl-6-methyl-3-[[2'-(1H-tetrazol-5-yl]biphenyl-4-yl]methyl ]-pyrimidine-4(3H)-one (Compound 3), M.P.:96.8 ~98.6C TLCR$_F$: 0.31(5% MeOH in CHCl$_3$) 1H NMR(CDCl$_3$): δ 0.91(t,3H), 1.26(t,3H), 1.31~1.45(m,2H), 1. 61~1.80 (mr,2H) , 2.31(s,3H), 2.67(t,2H), 3.76(q,2H), 3.81(s,2H), 3.99(q,2H), 5.26(s,2H), 7. 01~7.18 (n, 3H) , 7.20 ~7.28 (m, 1H) , 7.33~7.41(m,1H), 8.06(dd,1H).

EXAMPLE 4

2-n-butyl-5-heptamethyleniminothiocarbonyl-methyl-6-methyl-3-[[2'-(1H-tetrazol-5-yl)biphenyl-4-yl]methyl]-pyrimidine-4(3H)-one (Compound 4), M.P.: 104.2~107.3° C.; TLCR$_f$: 0.47(7% MeOH in CHCl$_3$) 1H NMR(CDCl$_3$): δ 0.83(t,3H), 1.21~1.30(m,2H), 1.4~1.70(m,8H), 1.71~1.95(m,4H), 2.21(.,3H), 2.53(t,2H), 3.60~3.88(H,4H), 4.02(s,2H), 5.15(s,2H), 6.98~7.09(s,5H), 7.22~7.58(m,3H), 7.77(dd,1H)

EXAMPLE 5

2-n-butyl-5-thiomorpholynothiocarbonylmethyl-6-methyl-3-[[2'-(1H-tetrazol-5-yl)-biphenyl-4-yl]methyl]-pyrimidine-4(3H)-one (Compound 5), M.P. 115.5~119.1° C.; TLCR$_f$: 0.33(7% MeOH in CHCl$_3$); 1H NMR(CDCl$_3$): δ 0.91(t,3H), 1.31~1.48(m,2H), 1.61~1.74(rm,2H), 2.30(s,3H), 2.65(t,2H), 2.72~2.84(m,4H), 3.81(s,2H), 4.22(t,2H), 4.59(t,2H), 5.25(s,2H), 7.03~7.15(m,5H), 7.35~7.61(m,3H), 8.00(dd,1H)

EXAMPLE 6

2-n-butyl-5-morpihoiynothiocarbonylmethyl-6-methyl-3-[[2'-(1H-tetrazol-5-yl)-biphenyl-4-yl]methyl ]-pyrimidine-4(3H)-one (Compound 6)

M.P. 91.2~94.3° C.; TLCR$_f$: 0.30(7% MeOH in CHCl$_3$); 1H NMR(CDCl$_3$): δ 0.92(t,3H), 1.23~1.48(m,2H), 1.63~1.81(m,2H), 2.34(s,3H), 2.69(t,52H), 2.68~2.82(m,4H), 3.85(s,2H), 3.97(t,2H), 4.34(t,2H), 5.27(s,2H), 7.05~7.20(m,5H), 7.35~7.65(m,3H), 8.05(dd,1H).

EXAMPLE 7

2-n-butyl-5-piperidinothiocarbonylmethyl-6-methyl-3-[[2'-(1H-tetrazol-5-yl)-biphenyl-4-yl]methyl) ]-pyrimidine-4(3H)-one (Compound 7), M.P.: 94.2~97.6° C.; TLCR$_f$: 0.37(5% MeOH in CHCl$_3$); 1H NMR(CDCl$_3$): δ 0.91(t,3H), 1.31~1.48(m,2H), 1.61~1.80(m,8H), 2.30(s,3H), 2.67(t,2H), 3.72~3.90(m,4H), 4.26(s,2H), 5.25(s,2H), 7.03~7.15(m,5H), 7.35~7.61(m,3H), 8.01(dd,1H)

EXAMPLE 8

2-n-butyl-5-pyrrolidinothiocarbonylmethyl-6-methyl-3-[[2'-(1H-tetrazol-5-yl)-biphenyl-4-yl]methyl]-pyrimidine-4(3H)-one (Compound 8)

M.P. 94.4~97.3° C.; TLCR$_f$: 0.26(5% MeOH in CHCl$_3$); 1H NMR(CDCl$_3$): δ 0.91(t,3H), 1.31~1.48(m,2H), 1.61~1.80(m,2H), 1.91~2.18(m,4H), 2.32(s,3H), 2.67(t,2H), 3.60~3.90(m,6H), 5.24(s,2H), 7.03~7.15(m,5H), 7.35~7.61(m,3H), 8.02(dd,1H).

EXAMPLE 9

2-n-butyl-5-azetidinothiocarbonylmethyl-6-methyl-3-[[2'-(1H-tetrazol-5-yl)-biphenyl-4-yl]methyl]-pyrimidine-4(3H)-one (Compound 9)

M.P.: 92.4~93.8° C.; TLCR$_f$: 0.24(5% MeOH in CHCl$_3$); 1H NMR(CDCl$_3$): δ 0.91(t,3H), 1.31~1.45(m,2H), 1.61~1.75(m,2H), 2.20~2.35(m,2H), 2.39(s,3H), 2.67(t,2H), 3.59(s,2H), 4.21(t,2H), 4.47(t,2H), 5.24(s,2H), 7.03~7.15 (m,4H), 7.18~7.25(m,1H), 7.35~7.61 (m,3H), 8.04(dd,1H).

EXAMPLE 10

2-n-butyl-5-(2'-aminothiocarbonylethyl)-6-methyl-3-[[(2'-(1H-tetrazol-5-yl)-biphenyl-4-yl]methyl ]-pyrimidine-4(3H)-one (Compound 10)

M.P.: 97.8~99.0° C.; TLCR$_f$: 0.43(5% MeOH in CHCl$_3$); 1H NMR(CDCl$_3$): δ 0.93(t,3H), 1.32~1.48 (m,2H), 1.62~1.80(m,2H), 2.40(s,3H), 2.60~2.80(m,4H), 2.87(t,2H), 5.27(s,2H), 7.10~7.25(m,4H), 7.35~7.65(m,4H), 8.10(dd, 1H)

EXAMPLE 11

2-n-butyl-5-(2'-dimethylaminothiocarbonylethyl)-6-methyl-3-[[2'-(1H-tetrazol-5-yl)-biphenyl-4-yl]methyl]-pyrimidine-4(3H)-one (Compound 11)

M.P.: 76.2~81.21° C.; TLCR$_f$: 0.21(5% MeOH in CHCl$_3$); 1H NMR(CDCl$_3$): δ 0.90(t,3H), 1.28~1.45(m,2H), 1.58~1.74(m,2H), 2.37(s,3H), 2.63(t,2H), 2.85~3.05(m,4H), 3.42(s,3H), 3.47(s,3H), 5.23(s,2H), 6.95~7.13(m,4H), 7.27~7.65(m,4H), 7.87(dd,1H)

EXAMPLE 12

2-n-butyl-5-(2'-diethylaminothiocarbonylethyl)-6-methyl-3-[[2'-(1H-tetrazol-5-yl)-biphenyl-4-yl]methyl]-pyrimidine-4(3H)-one (Compound 12)

M.P. 77.8~81.1° C.; TLCR$_f$: 0.37(5% MeOH in CHCl$_3$); 1H NMR(CDCl$_3$): δ 0.88(t,3H), 1.12~1.45(m,8H), 1.55~1.74(m,2H), 2.37(s,3H), 2.59(t,2H), 2.85~3.15(m,4H), 3.70(q,2H), 3.37(q,2H), 5.20(s,2H), 6.90~7.05(m,4H), 7.20~7.55(m,4H), 7.78(dd,1H).

EXAMPLE 13

2-n-butyl-5-(2'-thiomorpholynothiocarbonylethyl)-6-methyl-3-[[2'-(1H-tetrazol-5-yl)-biphenyl-4-yl]methyl]-pyrimidine-4(3H)-one (Compound 13)

M.P.: 80.1~83.3° C.; TLCR$_f$: 0.28(5% MeOH in CHCl$_3$); 1H NMR(CDCl$_3$): δ 0.91(t,3H), 1.30~1.45(m,2H), 1.60~1.70(m,2H), 2.39(s,3H), 2.55~2.90(m,8H), 2~97(t,2H), 4.22(t,2H), 4.58(t,2H), 7.04~7.25(m,5H), 7.35~7.42 (m,1H), 7.45~7.65(m,2H), δ .08(dd,1H).

EXAMPLE 14

2-n-butyl-5-(2'-morpholynothiocarbonylethyl)-6-methyl-3-[[2'-(1H-tetrazol-5-yl)-biphenyl-4-yl]methyl]-pyrimidine-4(3H)-one (Compound 14)

M.P.: 92.2~94.7 ° C.; TLCR$_f$: 0.39(7% MeOH in CHCl$_3$); 1H NMR(CDCl$_3$): δ 0.91(t,3H), 1.30~1.45 (m,2H), 1.60~1.75(m,2H), 2.39(s,3H), 2.67(t,2H), 2.88(t,2H), 3.05 (t,2H), 3.65~3.80(m,4H), 3.94(t,2H), 4.31(t,2H), 5.27(s,2H), 7.04~7.30(m,5H), 7.38~7.42(m,1H), 7.50~7.68(m,2H), 8.08(dd,1H).

The antagonistic activity of the compound (I) against the angiotensin II, which is prepared by the process according to a preferred embodiment of the invention, was evaluated with relation to rats. The results are shown in Table 1.

Experimental test I

In vivo Angiotensin II antagonism in conscious normotensive rats.

Male SD rats (Charles River Japan, 9 weeks, 300–350 g) were anesthetized with pentobarbital at 50 mg/kg i.p. Both the left femoral artery and the right femoral vein were cannulated. A heparin-filled catheter (50U/ml) was tunneled subcutaneously (s.c.) to the dorsal side of the neck and exteriorized.

Rats were permitted to recover overnight from anesthesia and allowed free access to water, but food was withheld.

The next day, the femoral artery catheter was connected to a pressure transducer (COBE 041-500-508, USA) coupled to a polygraph (GRASS Model 7, USA) to monitor arterial blood pressure. After an appropriate equilibration period, Angiotensin II (0.1 μg/kg) was injected in the femoral vein three times during the control period.

Test compounds were then administered orally (p.o.) at a constant volume of 2 ml/kg.

Angiotensin II challenges were repeated at set times thereafter.

$ID_{50}$ values, the dose of test compound necessary to produce 50% inhibition of Angiotensin II-induced pressor response, were calculated from peak inhibition percentage with several doses of test compound.

TABLE I

| COMPOUND NO. | $ID_{50}$(mg/kg, P.O.) |
|---|---|
| Compound 1 | >3.0 |
| Compound 2 | 1.10 |
| Compound 3 | <3.0 |
| Compound 4 | 3.10 |
| Compound 5 | <3.0 |
| Compound 6 | <3.0 |
| Compound 7 | <3.0 |
| Compound 8 | 0.93 |
| Compound 9 | 1.19 |

Experimental test II

Acute Toxicity Test

Respective 5 mice of ICR system, which was distributed from Korean Laboratory Animal Center, were bred in a polycarbonate breeding box at a breeding environment of 23±1° C. of temperature, 55±5% of humidity, 10–15 times/hr of evacuation, 12 hr cycle of fluorescent light luminance, and 150–300 Lux of illumination.

After observing the mice for one week of acclimation breeding period, only normal mice were selected for laboratory work. The mice were fed with sterilized feed for laboratory animals, which was made by Cheil Jedang Co., Ltd, and supplied with purified water to drink.

During the acclimation period, mice, who were evaluated to be healthy, were weighed and divided into groups randomly. Individual identification of laboratory animals was performed by indumentum pigment display and tag display per breeding box.

Establishment of dose was carried out according to a result of preliminary test in such a manner that a maximum dose group for both male and female was set to 5000 mg/kg and azeotropy was set to 1.71. Medium-high, medium and medium-low dose groups were respectively set as follows and a control group was administrated with physiological saline for injection.

TABLE II

| TESTING GROUP | DOSE (MG/KG) MALE | DOSE (MG/KG) FEMALE | ADMINISTRATION DOSE (ML/KG) | TOTAL TESTING ANIMALS MALE | TOTAL TESTING ANIMALS FEMALE |
|---|---|---|---|---|---|
| Control Group | 0 | 0 | 10 | 5 | 5 |
| Maximum Dose Group | 5000 | 5000 | 10 | 5 | 5 |
| Medium-high dose Group | 2924 | 2924 | 10 | 5 | 5 |
| Medium dose Group | 1710 | 1710 | 10 | 5 | 5 |
| Medium-low dose group | 1000 | 1000 | 10 | 5 | 5 |

Before administration of testing substances, body weight of the laboratory animals was in the range of 24–28 g in case of male and in the range of 19–28 g in case of female, respectively. The laboratory animals were aged 6 weeks.

Preparation of the testing substances was dissolved in physiological saline before administration. Dose was calculated according to the body weight which was measured before administration and dispensed by oral administration to a mouse who was in abrosia for 18 hours before testing.

Observation of clinical symptom such as general change, toxic symptom and mortality was performed for all laboratory animals once an hour during 6 hours after administration on the very administration day, and once a day from the next day to 14th day of administration.

Administration group, who was administered with testing substances, and the control group were weighed on the administration day, first, third, seventh, tenth and fourteenth days from the administration at a predetermined time for all animals who were alive.

After finish of the test, all animals were slightly anesthetized with ether and bleeding-killed. Appearance and internal organs of the animals were examined with naked eye carefully. Animals, who died during the text, were examined in the same manner.

TABLE III

Mortality and $LD_{50}$ value in mouse administered orally with compounds

| Test substance | Sex | Dose (mg/kg) | Days after treatment[a] 0 | 1 | 2 | 3...7...14 | Final mortality[b] | $LD_{50}$ (mg/kg) |
|---|---|---|---|---|---|---|---|---|
| Compound 2 | Male | 5000 | 0/5 | 0/5 | 0/5 | 0/5...0/5...0/5 | 0/5 | 5000 ↑ |
| | | 2924 | 0/5 | 0/5 | 0/5 | 0/5...0/5...0/5 | | |
| | | 1710 | 0/5 | 0/5 | 0/5 | 0/5...0/5...0/5 | | |
| | | 1000 | 0/5 | 0/5 | 0/5 | 0/5...0/5...0/5 | | |
| | | 0 | 0/5 | 0/5 | 0/5 | 0/5...0/5...0/5 | | |
| | Female | 5000 | 0/5 | 0/5 | 0/5 | 0/5...0/5...0/5 | 0/5 | 5000 ↑ |
| | | 2924 | 0/5 | 0/5 | 0/5 | 0/5...0/5...0/5 | | |
| | | 1710 | 0/5 | 0/5 | 0/5 | 0/5...0/5...0/5 | | |

TABLE III-continued

Mortality and LD$_{50}$ value in mouse administered orally with compounds

| Test substance | Sex | Dose (mg/kg) | Days after treatment[a] | | | | | | Final mortality[b] | LD$_{50}$ (mg/kg) |
|---|---|---|---|---|---|---|---|---|---|---|
| | | | 0 | 1 | 2 | 3 | 7 | 14 | | |
| Compound 8 | Male | 1000 | 0/5 | 0/5 | 0/5 | 0/5 | 0/5 | 0/5 | | |
| | | 0 | 0/5 | 0/5 | 0/5 | 0/5 | 0/5 | 0/5 | | |
| | | 5000 | 2/5 | 1/3 | 0/2 | 0/2 | 1/2 | 0/1 | 4/5 | 3167 |
| | | 2924 | 3/5 | 0/2 | 0/2 | 0/2 | 0/2 | 0/2 | 3/5 | |
| | | 1710 | 2/5 | 0/3 | 0/3 | 0/3 | 0/3 | 0/3 | 2/5 | |
| | | 1000 | 0/5 | 0/5 | 0/5 | 0/5 | 0/5 | 0/5 | 0/5 | |
| | | 0 | 0/5 | 0/5 | 0/5 | 0/5 | 0/5 | 0/5 | 0/5 | |
| | Female | 5000 | 4/5 | 0/1 | 0/1 | 0/1 | 0/1 | 0/1 | 4/5 | 4064 |
| | | 2924 | 2/5 | 0/3 | 0/3 | 0/3 | 0/3 | 0/3 | 2/5 | |
| | | 1710 | 0/5 | 0/5 | 0/5 | 0/5 | 0/5 | 0/5 | 0/5 | |
| | | 1000 | 0/5 | 0/5 | 0/5 | 0/5 | 0/5 | 0/5 | 0/5 | |
| | | 0 | 0/5 | 0/5 | 0/5 | 0/5 | 0/5 | 0/5 | 0/5 | |

[a]Values are expressed as death number/survival number of animal
[b]Values are expressed as death number/total number of animal

EXAMPLES 15 TO 28

Preparation of Tablet

The below ingredients (1) to (4) were mixed and granulated. To the granules magnesium stearate 5) was added, mixed and compressed to give a unit tablet (200 mg) (Example 15).

Similarly, tablets containing other compounds (2) to (14) of the invention were prepared (Examples 16 to 28).

TABLE IV

| COMPOSITION | WEIGHT (mg) |
|---|---|
| 1) Compound 1 | 40 |
| 2) Lactose | 30 |
| 3) Corn Starch | 100 |
| 4) Microcrystalline Cellulose | 25 |
| 5) Magnesium Stearate | 5 |
| Total | 200 |

EXAMPLES 29 TO 42

Preparation of Capsule

In a conventional way the ingredients of Table 2 were mixed, granulated and dispensed to give a unit capsule (200 mg) (Example 29).

Similarly, capsules containing other compounds (2) to (14) of the invention were prepared (Examples 30 to 42).

Industrial Applicability

According to the present invention, it is possible to obtain a novel compound of general formula (I) which is useful as antagonists against angiotensin II.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A pyrimidinone compound of formula (I) or pharmaceutically acceptable salts thereof:

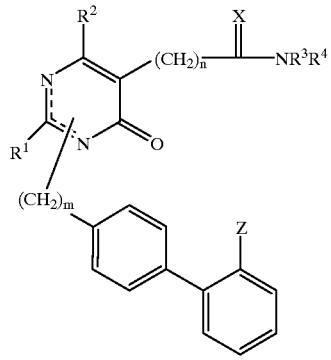

(I)

wherein:
R$^1$ is C$_1$~C$_4$ normal or side chain alkyl, cycloalkyl, and C$_1$-C$_4$ alkylalkoxy or C$_1$~C$_4$ alkylmercapto;
R$^2$ is H, halogen, C$_1$~C$_4$ alkl, or arylalkyl;
R$^3$, R$^4$ is same or different H, C$_1$~C$_4$ normal or side chain alkyl, cycloalkyl, carbocyclic aryl, arylalkyl, arylcarbonyl, C$_1$~C$_4$ alkoxycarbonyl, or aminocarbonyl, being optionally substituted by H, halogen, hydroxy, C$_1$~C$_4$ alkoxy, amino, alkylamino or dialkylamino (each alkyl having C$_1$~C$_5$), C$_1$~C$_4$ alkoxycarbonyl or carboxy;
R$^3$ and R$^4$ are together with N atom forming 4 to 8 membered heterocyclic ring, which can be further substituted with one or two substituents selected from the group consisting of cycloalkyl, carbocyclic aryl or arylalkyl, halogen, hydroxy, C$_1$~C$_4$ alkoxy, amino alkylamino or dialkylamnino (each alkyl residue having C$_1$~C$_5$), C$_1$~C$_4$ alkoxycarbonyl, carboxy or aminocarbonly, and C$_1$~C$_4$ normal or side chain alkyl being optionally substituted by H, wherein said heterocyclic ring can further include —O—, —S—, —SO—, —SO$_2$— or >N—R$^5$;
R$^5$ is H, C$_1$C$_4$ alkyl, carbocyclic aryl, arylalkyl, substituted alkenyl, pyridyl, pyrimidyl, C$_1$~C$_4$ alkyl or arylcarbonyl, C$_1$~C$_4$ alkyl or arylcarbonyl, C$_1$~C$_4$ alkoxy carbonyl, aminocarbonyl, CN or SO$_2$NR$^3$R$^4$;
X is S or >N—R$^5$; and
Z is CN, COOR$^3$, SO$_2$NR$^3$R$^4$ or tetrazol-5-yl radical having the formula:

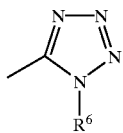 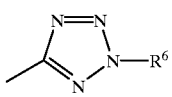

wherein R⁶ is H, t-butyl or triplifenylmethyl;

m is 1 or 2; and n is 1, 2, 3, 4, 5, and 6.

2. The compound or pharmaceutically acceptable salts thereof, according to claim 1, wherein:

R¹ is ethyl, n-propyl, n-butyl, cyclopropyl, ethoxyl or propoxyl; and

R² is H, halogen Or $C_1$~$C_4$ normal or side chain alkyl.

3. The compound or pharmaceutically acceptable salts thereof, according to claim 2, wherein:

R³, R⁴ is same or different H, methyl, ethyl, propyl or butyl, or R³ and R⁴ are together with N atom forming 4 to 8 membered heterocyclic ring, which can be further substituted with one or two substituents selected from the group consisting of cycloalkyl, carbocyclic aryl or arylalkyl, halogen, hydroxy, $C_1$~$C_4$ alkoxy, amino, alkylamino or dialkylamino (each alkyl residue having $C_1$~$C_5$), $C_1$~$C_4$ alkoxycarbonyl, carboxy or aminocarbonyl, and $C_1$~$C_4$ normal or side chain alkyl being optionally substituted by H, wherein said heterocyclic ring can further include —O—, —S—, —$SO_2$— or >N—R⁵; and R⁵ is H, $C_1$~$C_4$ alkyl, carbocyclic aryl, arylalkyl, substituted alkenyl, pyridyl, pyrimidyl, $C_1$~$C_4$ alkyl or arylcarbonyl, $C_1$~$C_4$ alkoxy carbonyl, aminocarbonyl, CN or $SO_2NR^3R^4$.

4. The compound or pharmaceutically acceptable salts thereof, according to claim 3, wherein:

R⁵ is H, $C_1$~$C_4$ alkyl, $C_1$~$C_4$ alkoxy carbonyl, aminocarbonyl, CN or $SO_2NR^3R^4$.

5. The compound or pharmaceutically acceptable salts thereof, according to claim 4, wherein:

Z is tetrazol-5-yl radical; and m is 1.

6. The compound or pharmaceutically acceptable salts thereof, according to claim 1, wherein said compound of formula (I) is the one selected from the group consisting of:

2-n-butyl-5-aminothiocarbonylmethyl-6-methyl-3-[[2'-(1H-tetrazol-5-yl)biphenyl-4-yl]methyl]-pyrimidine-4 (3H)-one (Compound 1), 2-n-butyl-5-dimethylaminothiocarbonylmethyl-6-methyl-3-[[(2'-(1H-tetrazol-5-yl)biphenyl-4-yl] methyl]-pyrimidine-4 (3H)-one (Compound 2), 2-n-butyl-5-diethylaminothiocarbonylmethyl-6-methyl-3-[[2'-(1H-tetrazol-5-yl)biphenyl-4-yl]methyl]-pyrimidine-4 (3H)-one (Compound 3), 2-n-butyl-5-heptamethyleniminothiocarbonyl methyl-6-methyl-3-[[(2'-(1H-tetrazol-5-yl)biphenyl-4-yl] methyl]-pyrimidine-4(3H)-one (Compound 4), 2-n-butyl-5-thiomorpholinothiocarbonylmethyl-6-methyl-3-[[(2'-(1H-tetrazol-5-yl)-biphenyl-4-yl] methyl]-pyrimidine-4 (3H)-one (Compound 5), 2-n-butyl-5-morpholynothiocarbonylmethyl-6-methyl-3-[[2'-(1H-tetrazol-5-yl)-biphenyl-4-yl]methyl]-pyrimidine-4 (3H)-one (Compound 6), 2-n-butyl-5-piperidinothiocarbonylmethyl-6-methyl-3-[[2'-(1H-tetrazol-5-yl)-biphenyl-4-yl]methyl]-pyrimidine-4 (3H)-one (Compound 7), 2-n-butyl-5-pyrrolidinothiocarbonylmethyl-6-methyl-3-[[2'-(1H-tetrazol-5-yl)-biphenyl-4-yl]methyl]-pyrimidine-4 (3H)-one (Compound 8), 2-n-butyl-5-azetidinothiocarbonylmethyl-6-methyl-3-[[2'-(1H-tetrazol-5-yl)-biphenyl-4-yl] methyl]-pyrimidine-4(3H)-one (Compound 9), 2-n-butyl-5-(2'-aminothiocarbonylethyl)-6-methyl-3-[[2'-(1H-tetrazol-5-yl)-biphenyl-4-yl] methyl]-pyrimidine-4(3H)-one (Compound 10), 2-n-butyl-5-(2'-dimethylaminothiocarbonylethyl)-6-methyl-3-[[2'-(1H-tetrazol-5-yl)-biphenyl-4-yl] methyl]-pyrimidine-4 (3H)-one (Compound 11), 2-n-butyl-5-(2'-diethylaminothiocarbonylethyl)-6-methyl-3-[[2'-(1H-tetrazol-5-yl)-biphenyl-4-yl] methyl]-pyrimidine-4(3H)-one (Compound 12), 2-n-butyl-5-(2'-thiomorpholynothiocarbonylethyl)-6-methyl-3-[[2'-(1H-tetrazol-5-yl)-biphenyl-4-yl] methyl]-pyrimidine-4 (3H)-one (Compound 13), and 2-n-butyl-5-(2'-morpholynothiocarbonylethyl)-6-methyl-3-[[2'-(1H-tetrazol-5-yl)-biphenyl-4-yl] methyl]-pyrimidine-4 (3H)-one (Compound 14).

7. The compound or pharmaceutically acceptable salts thereof, according to any one of claim 1 to claim 6, wherein said salts are inorganic salts selected from the group consisting of Sodium salts, Potassium salts, Calcium salts, Magnesium salts of corresponding pyrimidinone compound (I) or the mixture thereof.

8. The compound or pharmaceutically acceptable salts thereof, according to any one of claim 1 to claim 6, wherein said salts are organic salts of corresponding pyrimidinone compound (I).

9. A pharmaceutical composition containing a therapeutically effective amount of a compound of the present invention any one of claim 1 to claim 6 and pharmaceutical excipient.

10. A method of treating cardiovascular disease caused by binding angiotension II to its receptor, comprising administering to a subject in need thereof a compound according to any one of claim 1 to claim 6, said compound being in an amount of effective for treating the disease.

11. A process for preparing compound (I) which comprises the steps of reacting compound (II) with $P_4S_{10}$, bis (tricyclohexyltartar) sulfide or Lawesson's reagent in any one selected among benzene, dichloromethane or tetrahydrofuran,(wherein X is S):

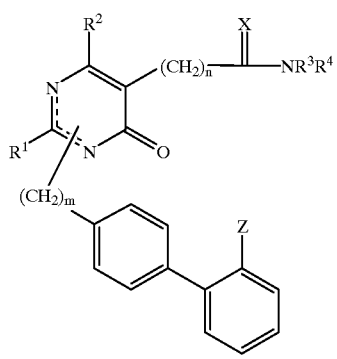

Compound Formula I

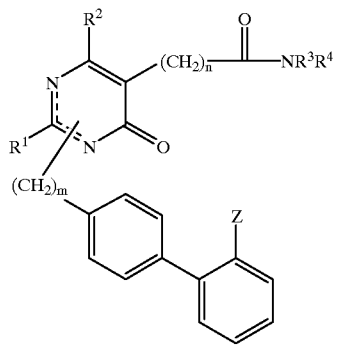

Compound Formula II (wherein $R^1$, $R^2$, $R^3$, $R^4$, $R^5$, Z, m and n have the meaning defined in claim 1.).

12. A process for preparing compound (I) which may be obtained by compound (II) by adding substituted amine after preparation of iminium intermediate by using a reagent selected from the group consisting of oxalylchloride, phosphorous oxychloride or ethyl chloroformate in a dissolvent selected among benzene, ether or tetrahydrofuran, wherein X is $NR^5$:

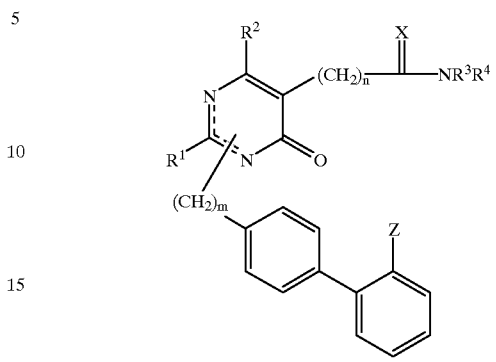

Compound Formula I

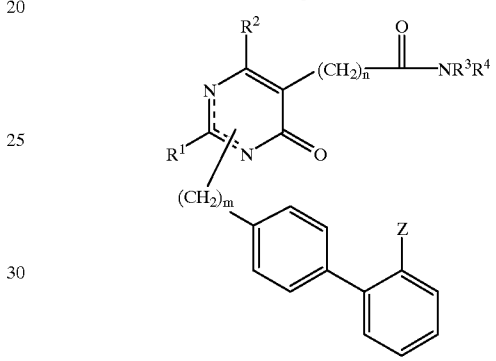

Compound Formula II (wherein $R^1$, $R^2$, $R^3$, $R^4$, $R^5$, z, m and n have the meaning defined in claim 1.).

* * * * *